(12) United States Patent
Avinash et al.

(10) Patent No.: US 7,929,746 B2
(45) Date of Patent: *Apr. 19, 2011

(54) SYSTEM AND METHOD FOR PROCESSING IMAGING DATA

(75) Inventors: Gopal B. Avinash, Menomonee Falls, WI (US); Kenny Kishan Israni, Chicago, IL (US); Baojun Li, Waukesha, WI (US)

(73) Assignee: General Electric Co., Schenectady, NY (US)

( * ) Notice: Subject to any disclaimer, the term of this patent is extended or adjusted under 35 U.S.C. 154(b) by 1165 days.

This patent is subject to a terminal disclaimer.

(21) Appl. No.: 11/464,103

(22) Filed: Aug. 11, 2006

(65) Prior Publication Data

US 2008/0037847 A1    Feb. 14, 2008

Related U.S. Application Data

(63) Continuation-in-part of application No. 11/463,845, filed on Aug. 10, 2006.

(51) Int. Cl.
  *G06K 9/00* (2006.01)
  *A61B 6/00* (2006.01)
(52) U.S. Cl. .................................... 382/131; 378/21
(58) Field of Classification Search .......... 382/128–134, 382/145, 159, 165, 170, 224, 225, 227; 378/4, 378/21–27, 46, 90, 92, 101, 140, 901; 600/407, 600/408, 425; 128/920, 925
See application file for complete search history.

(56) References Cited

U.S. PATENT DOCUMENTS

| | | | | |
|---|---|---|---|---|
| 5,375,175 A | * | 12/1994 | Kino et al. | 382/145 |
| 5,872,828 A | * | 2/1999 | Niklason et al. | 378/23 |
| 6,058,322 A | * | 5/2000 | Nishikawa et al. | 600/408 |
| 6,421,411 B1 | * | 7/2002 | Hsieh | 378/4 |
| 7,058,210 B2 | * | 6/2006 | Mundy et al. | 382/128 |
| 2005/0185824 A1 | | 8/2005 | Chen | |
| 2006/0210131 A1 | * | 9/2006 | Wheeler et al. | 382/128 |

* cited by examiner

*Primary Examiner* — Abolfazl Tabatabai

(57) ABSTRACT

A system and method includes using a point spread function based rule to classify regions in a dataset and processing the dataset based on the point spread function based classification.

15 Claims, 7 Drawing Sheets

SYSTEM AND METHOD FOR PROCESSING IMAGING DATA

CROSS-REFERENCE TO RELATED APPLICATIONS

This application is a continuation-in-part of and claims priority to U.S. patent application Ser. No. 11/463,845, filed Aug. 10, 2006, the disclosure of which is incorporated herein by reference.

BACKGROUND OF THE INVENTION

The present invention relates generally to x-ray systems and methods, and more particularly to systems and methods that utilize the classification of structures in a dataset to guide the selection of processing paths to reduce and eliminate blur from images.

Digital tomosynthesis is widely used for three-dimensional (3D) reconstruction of objects acquired from limited angle x-ray projection imaging using a movable x-ray tube and a stationary digital detector. It is a refinement of conventional linear tomography, which has been known since the 1930s. As with linear tomography, tomosynthesis suffers from the residual blur of objects outside the plane of interest. This tomographic blur, often caused by overlying anatomy, obscures detail in the plane of interest and limits the contrast enhancement of the projection image slices. Removing the overlying blurred anatomical structures improves contrast of in-plane structures by restricting the dynamic range of the image to a section of interest, as well as removing residual structures that may have frequency content similar to an object of interest in that section. At a fundamental level, the point spread function (PSF) of a tomosynthesis system characterizes the spread of blur in the imaging volume. The PSF of a tomosynthesis system is shift-variant in nature. However, completely eliminating blur is a non-trivial task. It is computationally complex and intensive because of the extent of the PSF, it is not easy to eliminate blur.

Tomosynthesis allows the retrospective creation of an arbitrary number of section images from a single pass of an x-ray tube. Projection images are acquired during an x-ray scan over a limited angle for reconstruction into full 3D volume images. To improve the presentation quality of the reconstruction slices, the tomosynthesis data is processed through a series of algorithms after reconstruction. Most prior art image processing techniques involve two-dimensional (2D) processing of the reconstructed image dataset without regard to the third dimension and prior knowledge of the imaging geometry. This is inadequate for tomosynthesis images where there can be out of focus high frequency components that can be sharpened by a presentation processing algorithm. These and many other artifacts have engineers, researchers and scientists interested in alternative ways of processing such images.

Since the true imaging geometry is represented using a 3D PSF of the dataset, in theory, it should be possible to use this information to improve the presentation processing of the reconstructed image dataset. Furthermore, if all points in the imaging volume can be classified based on whether they are in focus or out of focus, for example, in a certain plane, we can further adapt the processing algorithm based on the classification mask.

Therefore, there is a need for performing PSF based 3D presentation processing for a tomosynthesis dataset and to further adapt the processing based on a PSF based classification mask. This processing can also be used in a 3D multi-resolution processing framework.

BRIEF DESCRIPTION OF THE INVENTION

In an aspect, a method for processing a dataset based on a point spread function based classification.

In another aspect, a method for accessing a dataset; using a point spread function based rule to classify regions in the dataset; and processing the dataset based on the point spread function based classification.

In yet another aspect, a method providing an object to be scanned; scanning the object to obtain a dataset; using a point spread function based rule to classify regions in the dataset; and processing the dataset based on the point spread function based classification.

In still yet another aspect, a system includes an x-ray source, an x-ray detector positioned to receive x-rays emitted from the source, and a computer operationally coupled to the source and the detector. The computer is configured to process a dataset based on a point spread function based classification.

In a further aspect, a computer readable medium is provided that is embedded with a program that is configured to instruct a computer to process a dataset based on a point spread function based classification.

In another further aspect, a method comprising accessing a dataset, processing the dataset with multi-resolution presentation processing, and processing the dataset with a Z weighted function.

In yet another further aspect, a method comprising accessing a tomosynthesis imaging dataset, reconstructing the tomosynthesis imaging dataset, and processing the reconstructed tomosynthesis imaging dataset with multi-resolution presentation processing.

Various other features, objects, and advantages of the invention will be made apparent to those skilled in the art from the accompanying drawings and detailed description thereof.

DETAILED DESCRIPTION OF THE INVENTION

There are herein described systems and methods useful for imaging systems such as, for example, but not limited to an x-ray tomosynthesis system. The systems and methods are illustrated with reference to the figures wherein similar numbers indicate the same elements in all figures. Such figures are intended to be illustrative rather than limiting and are included herewith to facilitate explanation of an exemplary embodiment of the systems and methods of the invention. Although, described in the setting of an x-ray tomosynthesis system, it is contemplated that the benefits of the invention accrue to all imaging systems. One purpose of this disclosure is to provide a classification framework that decomposes a tomosynthesis dataset into multiple categories based on the nature of the PSF and to guide the selection of processing paths to reduce and eliminate blur from images.

Figure 1:
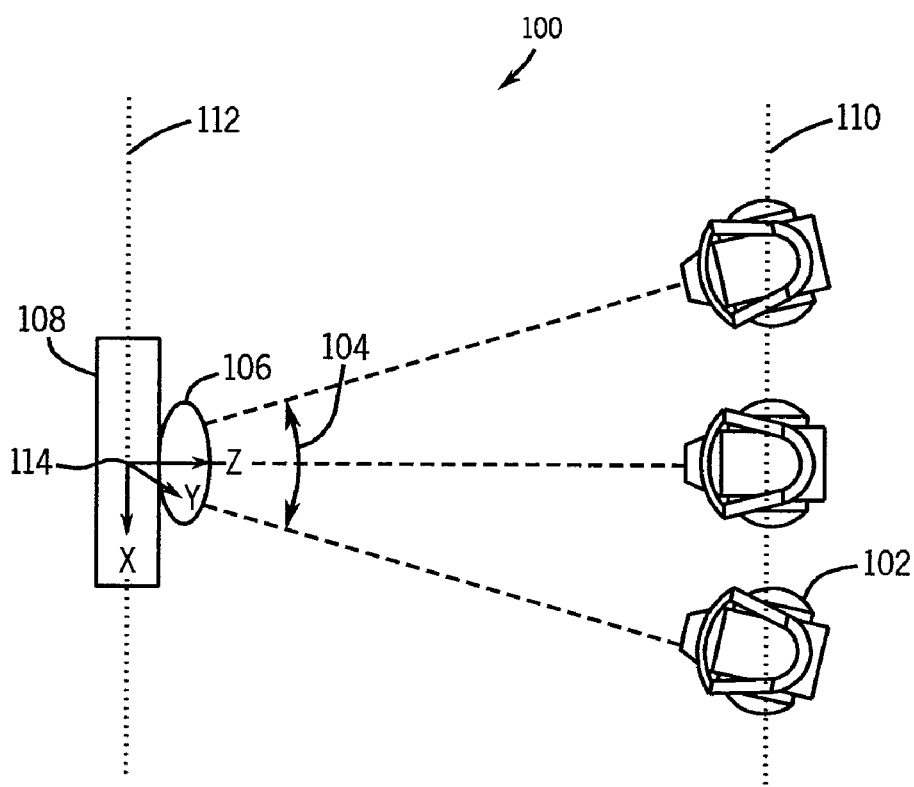
FIG. 1 is a diagram illustrating an exemplary x-ray imaging system.

Referring now to the drawings, FIG. 1 illustrates an exemplary x-ray tomosynthesis imaging system 100. The imaging system 100 includes an x-ray source 102, which subjects a structure under examination 106 to x-ray photons. As examples, the x-ray source 102 may be an x-ray tube, and the structure under examination 106 may be a human patient, test phantom, and/or other inanimate object under test.

The x-ray imaging system 100 also includes a detector 108 coupled to a processing circuit. The processing circuit (e.g., a CPU, a microcontroller, microprocessor, custom ASIC, or the like) is coupled to a memory or a data storage device, and a display device. The memory or data storage device (e.g., including one or more of a solid state memory device, magnetic memory device, optical memory device, disk storage device, tape storage device, floppy disk drive, hard disk drive, CD-ROM drive, DVD drive, magnetic optical disk (MOD) device, or any other digital device including a network connecting device such as an Ethernet device for reading instructions and/or data from a computer-readable medium, such as a floppy disk, or an other digital source such as a network or the Internet, as well as yet to be developed digital means, and the like) stores imaging data.

The memory may also store a computer program including instructions executed by the processing circuit to implement the functions described herein. The processing circuit provides an image for display on a device. As described in further detail herein, the image may representative of different structures (e.g., soft-tissue, bone). The detector 108 may be a flat panel solid-state image detector, for example, although conventional film images stored in digital form in the memory may also be processed. In one embodiment, the processing circuit executes instructions stored in firmware (not shown). Generally, a processor is programmed to execute the processes described below.

The tomosynthesis imaging process includes a series of projection x-ray images that are taken from different angles through the object 106 under examination. An arbitrary number of discrete projection images are acquired over a limited angular range 104 by arc rotation or linear translation of the x-ray tube 102. In the embodiment shown in FIG. 1, the motion of the x-ray tube 102 lies in a plane 110 parallel to the plane 112 of the detector 108. After acquiring the projection image datasets, application software is used to reconstruct the image slices. A coordinate system 114 is also shown in FIG. 1 to illustrate the X, Y, and Z directions.

Of course, the methods described herein are not limited to practice in system 100 and can be utilized in connection with many other types and variations of imaging systems. In one embodiment, the processing circuit is a computer that is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits. Although the herein described methods are described in a human patient setting, it is contemplated that the benefits of the invention accrue to non-human imaging systems such as those systems typically employed in small animal research.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also, as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image.

Although the herein described methods are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center.

In multi-resolution processing, the representation and analysis of images at more than one resolution is performed. It provides computational simplicity and flexibility. In addition, features that might go undetected at one resolution may be easy to spot at another resolution. This multi-resolution processing technique is represented in FIG. 2.

Figure 2:
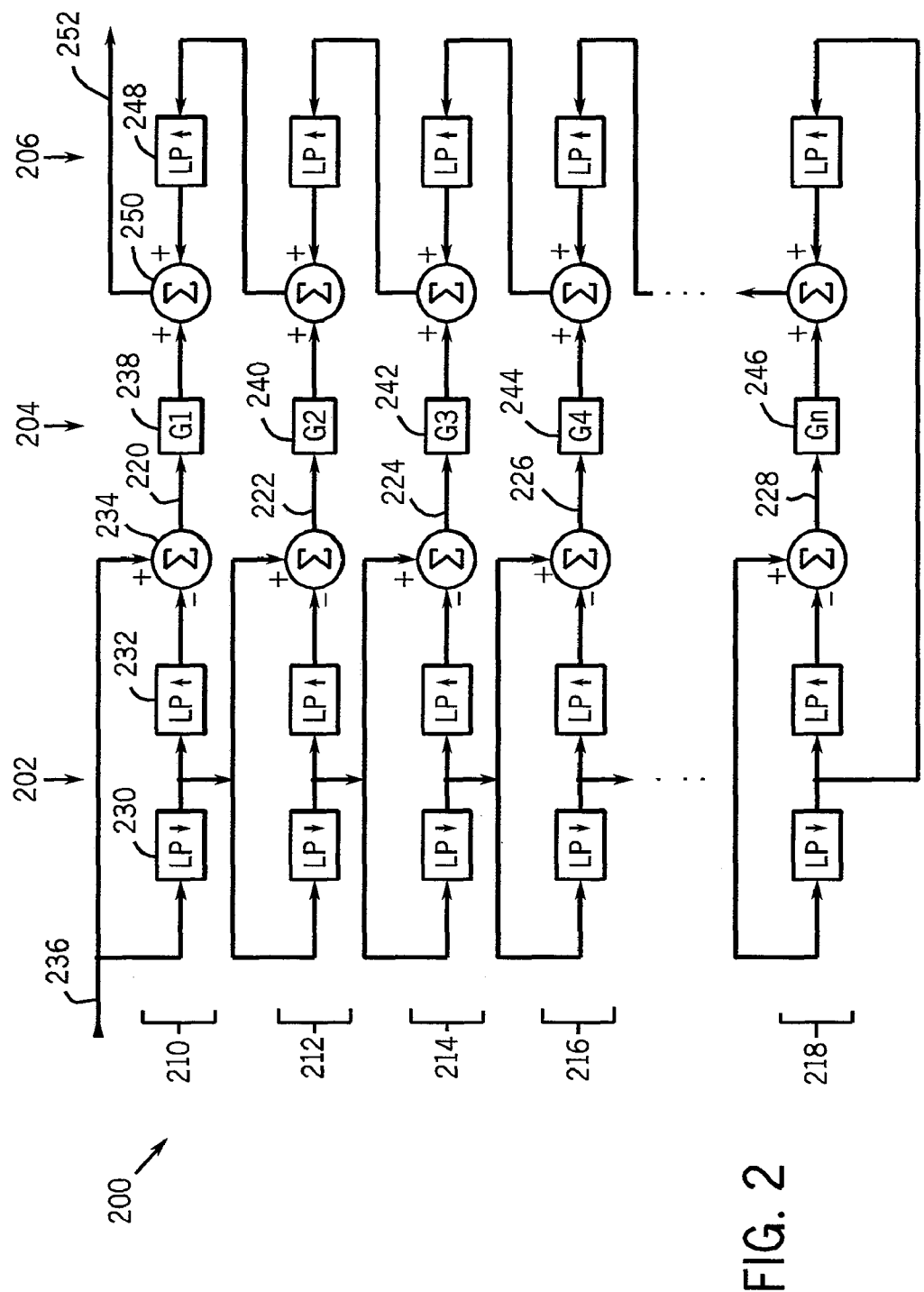
FIG. 2 is a diagram illustrating an image decomposition sequence for separating an image into decomposed images referenced by desired frequency bands.

FIG. 2 illustrates a filtering sequence 200 for spatially selective enhancement of an image. The example in FIG. 2 describes a two-dimensional filtering sequence (2D), however, a similar filtering sequence can be accomplished for other dimensions as well, including a one-dimensional (1D) filtering sequence or a three-dimensional (3D) filtering sequence. The filtering sequence includes a decomposition phase 202, an enhancement phase 204, and a recomposition phase 206. The decomposition phase 204 involves progressive decomposition of the image data into a series of spatial frequency images of progressively lower spatial frequency. As used herein, the term spatial frequency relates generally to the number of individual image components within a defined image area. Through the progressive decomposition of the image, the filtering sequence 200 generates a series of decomposed images having different spatial frequencies. Each of these images is then enhanced by application of a gain image during enhancement phase 204. The resulting images are then recombined during recomposition phase 206 to complete an enhanced image. The individual processing of the different spatial frequency levels of the decomposed images is represented in FIG. 2 by reference numerals 210, 212, 214, 216 and 218, with 218 being a final level of decomposition and processing. As noted, each progressive step or level produces an intermediate image having a progressively lower spatial frequency, as noted at reference numerals 220, 222, 224, 226, and 228.

As shown in FIG. 2, processing blocks for each spatial frequency level in decomposition phase include a decimator 230 and an interpolator 232, represented by low-pass filters (only the filters of the highest spatial frequency level 210 being labeled in FIG. 2). These filters progressively combine data representing neighboring pixels of the immediately preceding image level in a manner generally known in the art. The filters output a first, filtered image which is employed in subsequent decomposition levels, as well as a second image which is subtracted from the input image for that spatial frequency level at a summer 234. Thus, at a highest level 210, the original processed image data 236 is fed to the decimating low pass filter 230, as well as to summer 234. The original image data is filtered at blocks 230 and 232, with the output of block 230 being passed on as input data to level 212. In this manner, the original processed image data is decomposed into the progressively lower spatial frequency images. In an embodiment, each subsequent step or level in the decomposition phase produces an image which is half the size of the input image for that level. However, other reduction rates may be employed. Moreover, while the decomposition phase filtering may terminate at any desired level, in a present embodiment, such filtering is carried out until a single pixel (1×1) image is attained at lowest level 218.

The filtering sequence 200 then proceeds by applying (e.g., multiplying) each of the spatial frequency images by a gain image in enhancement phase 204. The gain images, designated in FIG. 2 by the numerals 238, 240, 242, 244, and 246, are assigned values which enhance specific features of the image, such as edges. Moreover, certain of the gain images are generated from data from lower spatial frequency levels. Thus, gain image 238, designated G1, is generated from image 220 resulting from the decomposition phase at level 210. Similarly, gain image 240, designated G2, is generated from image 222 resulting from processing at level 212. Any suitable number of levels in the filtering sequence 200 may employ such lower frequency-based gain images. For example, it has been found that in an image having original dimensions of 2048×2048 pixels, such lower spatial frequency-based gain images produce satisfactory edge enhancement when used at the first three levels of decomposition, such as levels 210, 212, and 214 in FIG. 2. Other lower levels may also employ this technique, or may be multiplied by a gain image having values of unity, or other values, either greater or less than unity.

Following application of the gain images at enhancement phase 204, the resulting enhanced images are recombined in recomposition phase 206. As shown in FIG. 2, each step or level in the recomposition phase includes interpolation of output data from an immediately preceding (i.e., lower) level in a block 248 (see level 210 in FIG. 2). The resulting image is added to the enhanced image in a summer 250 at each level. The resulting enhanced and recomposed image data is then forwarded to the next (i.e., higher) level, until a recomposed enhanced image 252 of the original dimensions is obtained.

It should be noted, that in particular applications, the image data need not be fully decomposed or recomposed to the lowest levels. For example, where a series of lower spatial frequency images are to have a similar gain applied in phase 204, decomposition may be stopped at that level. The gain is then applied to the image at the terminal level, and recomposition may begin. Similarly, while as noted above, the higher level gains are derived from lower spatial frequency images resulting from decomposition, these could also be obtained based upon recomposed images from a lower spatial frequency level (i.e., following application of the gain images during enhancement phase 204).

In an embodiment, the lower spatial frequency-based gains are derived as follows. Following decomposition of the original filtered image data, a processing circuit applies an algorithm which may be expressed as:

$$G_i(x,y) = \max(1.0, E_i * S(O_j(x,y))),$$

where $G_i(x,y)$ is the value for each pixel in the gain image of level i to be determined; $E_i$ is a user-defined edge strength value greater than 1.0; S is a spatial sensitivity function which may be set by the user; and $O_j(x,y)$ is the value of each pixel in a lower spatial frequency level image j. It should be noted, thus, that the foregoing algorithm effectively maintains a value of unity in the derived gain images when the resulting computed value is less than unity. Also, the algorithm permits the user to effectively define a desired edge strength value, tending to increase or decrease the relative sharpness of the edges and the recomposed enhanced image. Similarly, a spatial sensitivity function may be selected by the user to regulate the amount of influence in the gain calculation exerted by values of the lower spatial frequency image. The spatial sensitivity function could include linear functions, piecewise linear functions, a sigmoidal function, and so forth. In a present embodiment, the values of S resulting from the function S may be set anywhere between 0 and 1. Moreover, the edge strength value or the spatial sensitivity function, or both, may be unique to specific spatial frequency levels (i.e., unique to individual levels 210, 212, and 214 in FIG. 2). Also, the particular level at which such spatial frequency-based gain images is derived may be a parameter which is user configurable. Thus, the user may select spatial frequency-based enhancement for one, two, three, or more levels, depending upon the enhancement desired and the frequency levels at which useful information or noise is anticipated.

Within the multi-resolution framework, a set of tomosynthesis reconstructed slices is considered as one of the inputs. The other input includes a PSF based classified mask corresponding to multiple regions where in each region is a classification type. An embodiment as described in U.S. patent application Ser. No. 11/463,845 uses a PSF rule to classify regions of different intensity profiles. As an example, four classification types based on analyzing the nature of intensity profiles are: 1) in focus, 2) out of focus, 3) background, and 4) low frequency as described in U.S. patent application Ser. No. 11/463,845. This PSF based classified mask was numerically coded to identify the distinct regions: 1) m=1 for in focus data, 2) m=2 for out of focus data, 3) m=3 for background data, and 4) m=4 for low frequency data, where m denotes the value of each pixel in the mask. These inputs are made to be of the same resolution using up sampling (recomposition) or down sampling (decomposition) methods. Once the inputs are of the same resolution, several different methods can be used to process the data.

A novel methodology is presented for 3D processing of tomosynthesis data based on the PSF. There are several forms that the methodology can take while trading off computational efficiency and accuracy. Below are some methodology examples.

Example 1

Figure 3:
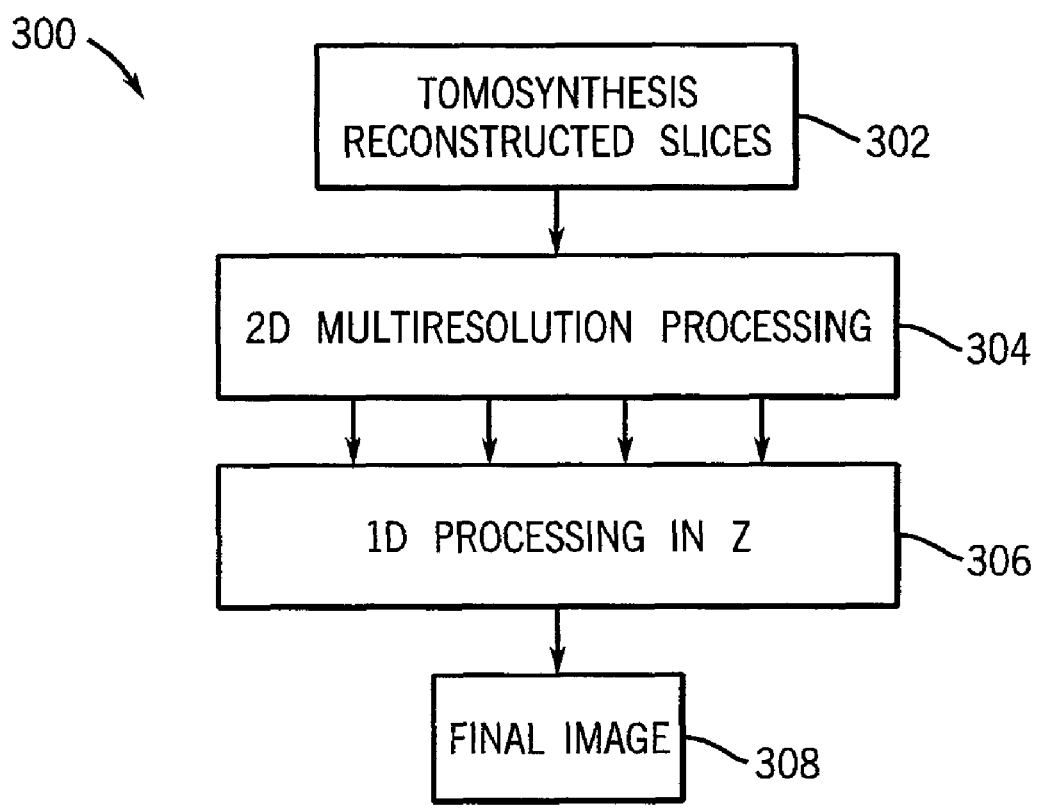
FIG. 3 is a flow diagram illustrating an exemplary embodiment of processing an imaging dataset.

A method 300 of processing an imaging dataset uses traditional 2D multi-resolution presentation processing and a one-dimensional (1D) Z weighted function 306 derived from the PSF along the mid-line of the 3D PSF. FIG. 3 is a flow diagram illustrating the method 300. This method 300 involves the following steps: 1) reconstructing image slices from acquired projection images 302; 2) performing traditional 2D multi-resolution presentation processing (not making use of any PSF classified regions) on each image slice to obtain a presentation processed image slice 304; 3) at each point on the presentation processed image slice data, determining a PSF based 1D Z weighted profile along the mid-line of the PSF; and 4) using the PSF based 1D Z weighted profile for the 1D Z weighted processing along the profile direction (not making use of any PSF classified regions) 306 to obtain an enhanced final image 308, wherein the 1D Z weighted processing can be a sharpening operation to mitigate blur.

Example 2

Figure 4:
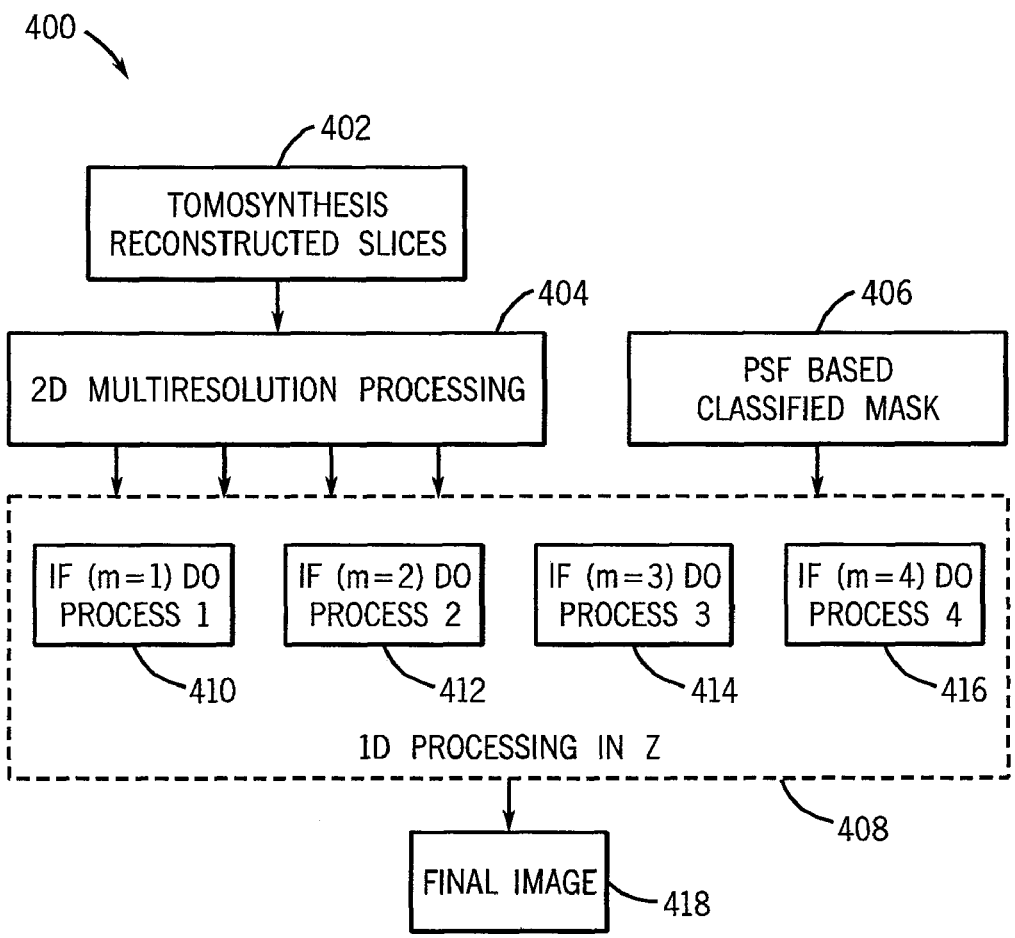
FIG. 4 is a flow diagram illustrating another exemplary embodiment of processing an imaging dataset.

A method 400 of processing an imaging dataset uses traditional 2D multi-resolution presentation processing, a PSF based classification mask 406, and a 1D Z weighed function 408 derived from the PSF and the shape of the 3D PSF. The 1D Z weighed processing 408 making use of PSF classified regions 410, 412, 414, 416. FIG. 4 is a flow diagram illustrating the method 400. This method 400 involves the following steps: 1) reconstructing image slices from acquired projection images 402; 2) performing traditional 2D multi-resolution presentation processing (not making use of any PSF classified regions) on each image slice to obtain a presentation processed image slice 404; 3) at each point on the presentation processed image slice data, determining a PSF based 1D Z weighted profile along the mid-line of the PSF; and 4) adaptively using the PSF based 1D Z weighted profile for the 1D Z weighted processing 408 along the profile direction based on a prior classification type 406 (making use of PSF classified regions 410, 412, 414, 416) to obtain an enhanced final image 418. The 1D Z weighted processing 408 can be a sharpening operation to mitigate blur. The sharpening strength can be varied based on the classification type.

Example 3

Figure 5:
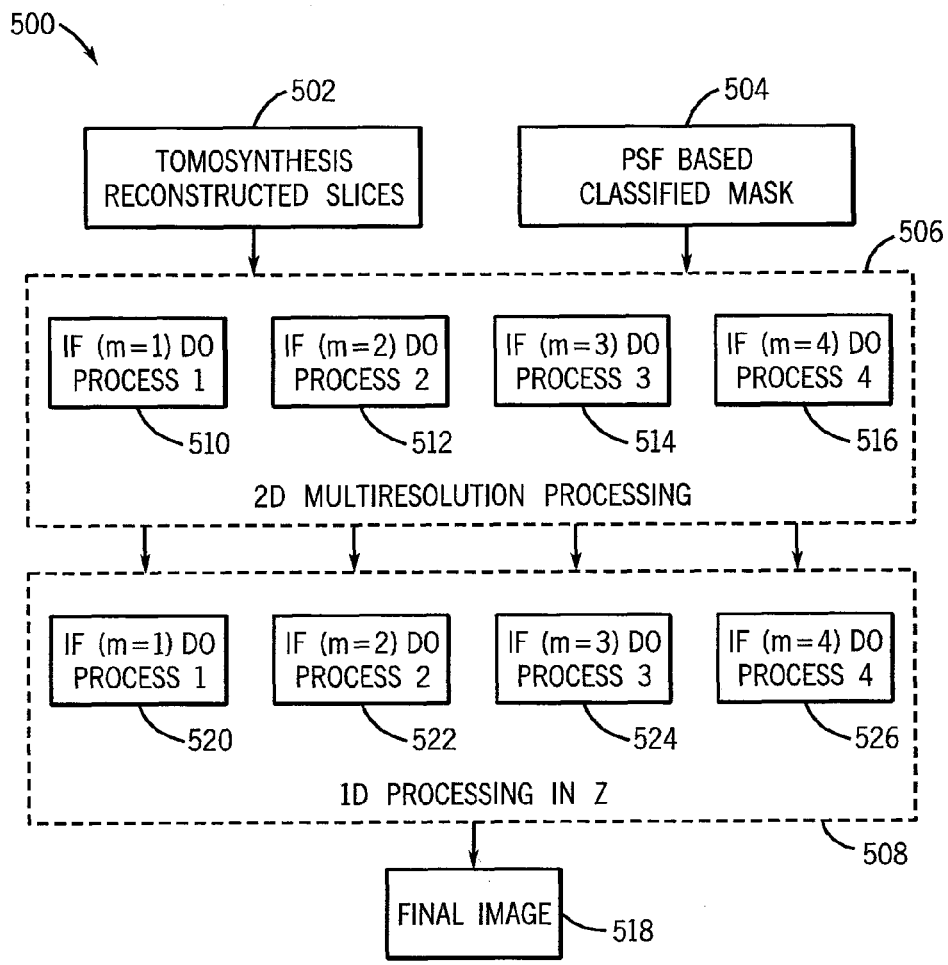
FIG. 5 is a flow diagram illustrating yet another exemplary embodiment of processing an imaging dataset.

A method 500 of processing an imaging dataset uses a PSF based classification mask 504 for both traditional 2D multi-resolution presentation processing 506 and 1D Z weighted processing 508 along the PSF mid-line profile. The traditional 2D multi-resolution presentation processing 506 making use of PSF classified regions 510, 512, 514, 516. The 1D Z weighted processing 508 making use of PSF classified regions 520, 522, 524, 526. FIG. 5 is a flow diagram illustrating the method 500. This method 500 involves the following steps: 1) reconstructing image slices from acquired projection images 502; 2) adaptively performing traditional 2D multi-resolution presentation processing on each image slice based on a prior classification type 504 (making use of PSF classified regions 510, 512, 514, 516) to obtain a presentation processed image slice 506 (note that this adaptive processing is in addition to other traditional adaptive processing that the traditional technique may already have); 3) at each point on the presentation processed image slice data, determining a PSF based 1D Z weighted profile along the mid-line of the PSF; and 4) adaptively using the PSF based 1D Z weighted profile for the 1D Z weighted processing 508 along the profile direction based on a prior classification type 504 (making use of PSF classified regions 520, 522, 524, 526) to obtain an enhanced final image 518. The 1D Z weighted processing can be a sharpening operation to mitigate blur. The sharpening strength can be varied based on the classification type. Different processing algorithms can be applied to different regions in the mask. For example, in focus structures can be sharpened while the effect of out of focus details can be attenuated. The resultant dataset can later be sampled to achieve the desired resolution.

Example 4

Figure 6:
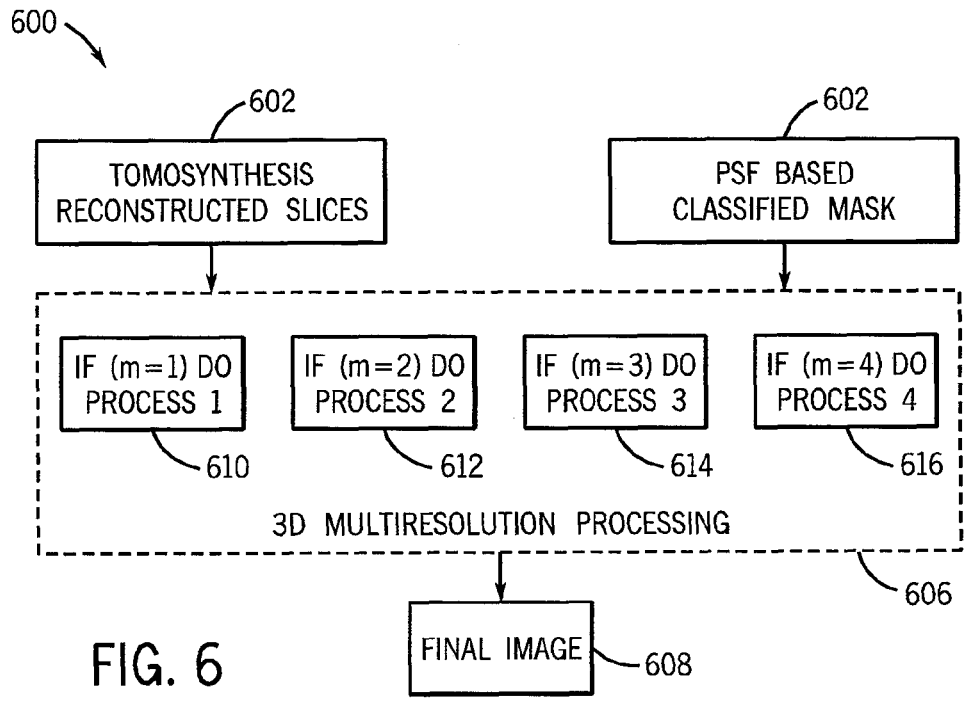
FIG. 6 is a flow diagram illustrating still another exemplary embodiment of processing an imaging dataset.

A method 600 of processing an imaging dataset uses a PSF based classification mask 604 with 3D multi-resolution presentation processing 606. The 3D multi-resolution presentation processing 606 making use of PSF classified regions 610, 612, 614, 616. FIG. 6 is a flow diagram illustrating the method 600. This method 600 involves the following steps: 1) reconstructing image slices from acquired projection images 602; 2) adaptively performing 3D multi-resolution presentation processing on each image slice based on a prior classification type 604 (making use of PSF classified regions 610, 612, 614, 616) to obtain a presentation processed image slice 606 and an enhanced final image 608, wherein different processing algorithms may be applied to different regions of the coded mask.

Example 5

Figure 7:
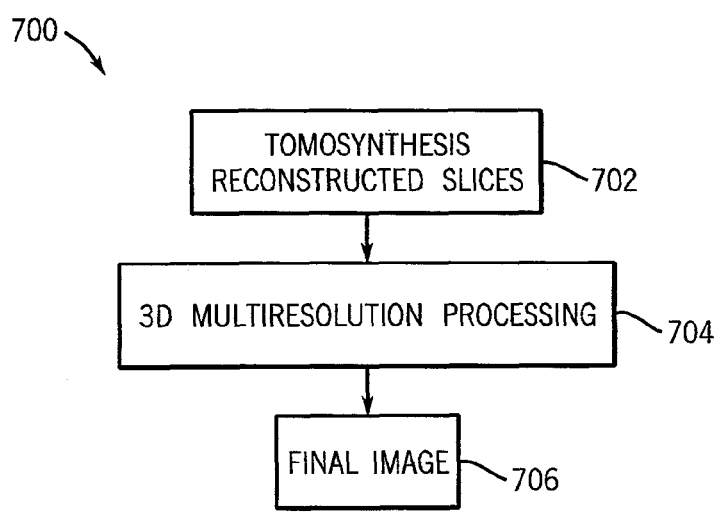
FIG. 7 is a flow diagram illustrating still yet another exemplary embodiment of processing an imaging dataset.

A method 700 of processing a tomosynthesis imaging dataset using traditional 3D multi-resolution presentation processing 704 (not making use of any PSF classified regions). FIG. 7 is a flow diagram illustrating the method 700. This method 700 involves the following steps: 1) reconstructing tomosynthesis image slices from acquired projection images 702; and 2) performing traditional 3D multi-resolution presentation processing 704 (not making use of any PSF classified regions) on each image slice to obtain an enhanced final image 706.

Example 6

Figure 8:
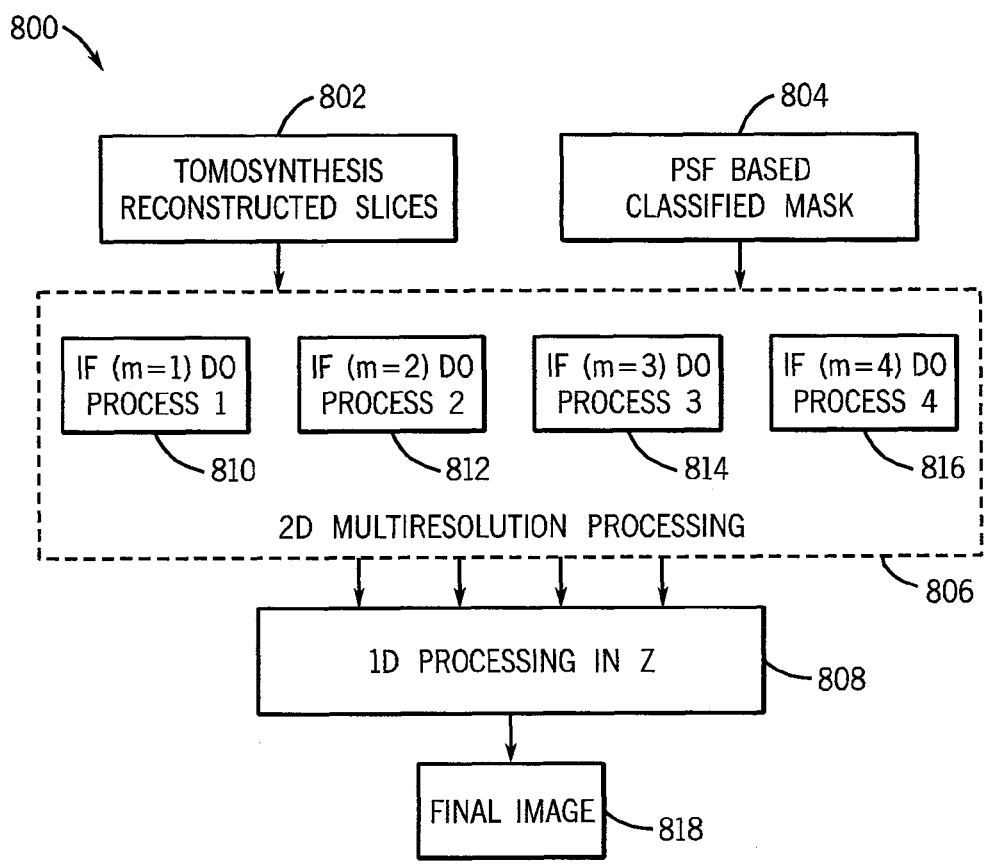
FIG. 8 is a flow diagram illustrating an exemplary embodiment of processing an imaging dataset.

A method 800 of processing an imaging dataset uses a PSF based classification mask 804 for traditional 2D multi-resolution presentation processing 806 and 1D Z weighted processing 808 along the PSF mid-line profile. The traditional 2D multi-resolution presentation processing making use of PSF classified regions 810, 812, 814, 816. The 1D Z weighted processing 808 not making use of any PSF classified regions. FIG. 8 is a flow diagram illustrating the method 800. This method 800 involves the following steps: 1) reconstructing image slices from acquired projection images 802; 2) adaptively performing traditional 2D multi-resolution presentation processing on each image slice based on a prior classification type 804 (making use of PSF classified regions 810, 812, 814, 816) to obtain a presentation processed image slice 806 (note that this adaptive processing is in addition to other traditional adaptive processing that the traditional technique may already have); and 3) at each point on the presentation processed image slice data, determining a PSF based 1D Z weighted profile along the mid-line of the PSF; and 4) using the PSF based 1D Z weighted profile for the 1D Z weighted processing 808 along the profile direction (not making use of any PSF classified regions) to obtain an enhanced final image 818, wherein the 1D Z weighted processing can be a sharpening operation to mitigate blur.

In summary, many different forms can be created based on the general framework described herein. These forms arise since one can process adaptively or non-adaptively in one or more dimensions. In addition to the traditional image-based adaptation of processing, this invention discloses a novel PSF based classification to adapt the processing for presentation.

One technical effect is that the herein described method and system provide the ability to classify structures (i.e., regions) based on the PSF and then one is able to selectively process the data differently for each different class if desired. This improved ability to process imaging data leads to less artifacts and/or blurring in the final reconstructed images.

Exemplary embodiments are described above in detail. The assemblies and methods are not limited to the specific embodiments described herein, but rather, components of each assembly and/or method may be utilized independently and separately from other components described herein.

While the invention has been described with reference to various embodiments, those skilled in the art will appreciate that certain substitutions, alterations and omissions may be made to the embodiments without departing from the spirit of the invention. Accordingly, the foregoing description is meant to be exemplary only, and should not limit the scope of the invention as set forth in the following claims.

What is claimed is:

1. A computer readable medium embedded with a program configured to instruct a computer to multi-resolution process a tomosynthesis dataset based on a point spread function based classification.

2. The computer readable medium of claim 1, wherein the classification is into classes comprising a background class, an in focus class, an out of focus class, and a low frequency class.

3. The computer readable medium of claim 1, wherein the program is further configured to use a point spread function based rule to classify regions of different intensity profiles in the tomosynthesis dataset.

4. The computer readable medium of claim 1, wherein the multi-resolution processing comprises a decomposition phase, the decomposition phase comprising progressive decomposition of the tomosynthesis data into a series of spatial frequency images of progressively lower spatial frequency.

5. A system, comprising:
an x-ray source;
an x-ray detector positioned to receive x-ray emitted from the source; and
a computer operationally coupled to the source and the detector, the computer configured to multi-resolution process a tomosynthesis dataset based on a point spread function based classification.

6. The system of claim 5, wherein the classification is into classes comprising a background class, an in focus class, an out of focus class, and a low frequency class.

7. The system of claim 5, wherein the computer provides a platform for 3D adaptive deblurring of tomosynthesis datasets.

8. The system of claim 5, wherein the computer is configured to provide a PSF based adaptive processing of tomosynthesis images.

9. The system of claim 5, wherein the process covers any type of multi-resolution processing for tomosynthesis images.

10. The system of claim 5, wherein the computer is further configured to use a point spread function based rule to classify regions of different intensity profiles in the tomosynthesis dataset.

11. The system of claim 5, wherein the multi-resolution processing comprises a decomposition phase, the decomposition phase comprising progressive decomposition of the tomosynthesis data into a series of spatial frequency images of progressively lower spatial frequency.

12. A method, comprising:
scanning an object to obtain a tomosynthesis dataset;
using a point spread function based rule to classify regions in the tomosynthesis dataset; and
performing multi-resolution processing of the tomosynthesis dataset based on the point spread function based classification.

13. The method of claim 12, wherein the point spread function based rule is used to classify regions of different intensity profiles in the tomosynthesis dataset.

14. The method of claim 12, wherein performing multi-resolution processing comprises generating a series of decomposed images having different spatial frequencies.

15. The method of claim 12, wherein performing multi-resolution processing comprises a filtering sequence for spatially selective enhancement of the tomosynthesis data.

* * * * *